(12) United States Patent
Wang

(10) Patent No.: US 10,119,150 B2
(45) Date of Patent: *Nov. 6, 2018

(54) FEEDER-FREE DERIVATION OF HUMAN-INDUCED PLURIPOTENT STEM CELLS WITH SYNTHETIC MESSENGER RNA

(71) Applicant: Allele Biotechnology & Pharmaceuticals, Inc., San Diego, CA (US)

(72) Inventor: Jiwu Wang, La Jolla, CA (US)

(73) Assignee: Allele Biotechnology & Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/292,317

(22) Filed: May 30, 2014

(65) Prior Publication Data

US 2014/0349401 A1 Nov. 27, 2014

Related U.S. Application Data

(63) Continuation-in-part of application No. 13/893,166, filed on May 13, 2013.

(60) Provisional application No. 61/646,292, filed on May 13, 2012.

(51) Int. Cl.
| | |
|---|---|
| *C12N 15/85* | (2006.01) |
| *C12N 5/074* | (2010.01) |
| *C12N 15/11* | (2006.01) |
| *C07K 14/47* | (2006.01) |
| *C07K 14/475* | (2006.01) |

(52) U.S. Cl.
CPC .......... *C12N 15/85* (2013.01); *C07K 14/4702* (2013.01); *C07K 14/475* (2013.01); *C12N 5/0696* (2013.01); *C12N 15/111* (2013.01); *C07K 2319/01* (2013.01); *C12N 2310/14* (2013.01); *C12N 2320/30* (2013.01); *C12N 2501/602* (2013.01); *C12N 2501/603* (2013.01); *C12N 2501/605* (2013.01); *C12N 2501/608* (2013.01); *C12N 2506/1307* (2013.01); *C12N 2510/00* (2013.01)

(58) Field of Classification Search
CPC .... C12N 15/85; C12N 5/0696; C12N 15/111; C12N 2310/14; C12N 2320/30; C12N 2501/602; C12N 2501/603; C12N 2501/605; C12N 2501/608; C12N 2506/1307; C12N 2510/00; C07K 14/4702; C07K 14/475; C07K 2319/01
See application file for complete search history.

(56) References Cited

U.S. PATENT DOCUMENTS

| | | | |
|---|---|---|---|
| 7,033,828 B2 | 4/2006 | Takaku et al. | |
| 8,497,124 B2 | 7/2013 | Angel et al. | |
| 9,127,248 B2 | 9/2015 | Angel et al. | |
| 9,399,761 B2 | 7/2016 | Angel et al. | |
| 9,562,218 B2 | 2/2017 | Angel et al. | |
| 9,695,401 B2 | 7/2017 | Angel et al. | |
| 9,879,228 B2 | 1/2018 | Angel et al. | |
| 9,969,983 B2 | 5/2018 | Angel et al. | |
| 2009/0191159 A1* | 7/2009 | Sakurada | C12N 5/0696 424/93.7 |
| 2012/0207744 A1 | 8/2012 | Mendlein et al. | |
| 2013/0302295 A1 | 11/2013 | Wang et al. | |

FOREIGN PATENT DOCUMENTS

| | | | | |
|---|---|---|---|---|
| CA | 2770412 A1 | * | 2/2011 | ........... C12N 5/0696 |
| WO | WO2010/057614 | | 5/2010 | |
| WO | WO2011/142832 | | 11/2011 | |
| WO | WO-2012/012708 A1 | | 1/2012 | |
| WO | WO 2013/126813 A1 | | 8/2013 | |
| WO | WO 2013/173248 A2 | | 11/2013 | |

OTHER PUBLICATIONS

Mandal et al., Nature Protocols, 8(3): 568-582, Feb. 21, 2013.*
Liu et al., Plos ONE, 8(6): 1-11, 2013.*
Navara et al., Cellular Reprogramming, 15(6): 495-502, 2013.*
Weintraub. Gene Dev. 5:1377-1386, 1991.*
Breton et al., Stem Cells and Development, 22(4): 611-621, 2013.*
Liao et al., Cell Research, 18: 600-603, 2008.*
Wang et al., EMBO Reports, 12(4): 2011, including Supplemental Materials, pp. 1-25.*
Wang et al., Protein Cell, 3(1): 51-59, Jan. 1, 2012.*
Lindstrom et al., PLoS One, e6997, 4(9): 1-9, 2009.*
Wang Declaration, filed Sep. 26, 2017, in U.S. Appl. No. 13/893,166, pp. 1-17.*
International Search Report in International Application No. PCT/US2015/033275, dated Oct. 16, 2015, in 4 pages.
Gai et al., "Generation and characterization of functional cardiomyocytes using induced pluripotent stem cells derived from human fibroblasts," *Cell Biol. Int.*, 2009, 33:1184-1193.
Grigoriadis et al., "Directed differentiation of hematopoietic precursors and functional osteoclasts from human ES and iPS cells," *Blood*, 2010, 115(14):2769-2776.

(Continued)

*Primary Examiner* — Thaian N Ton
(74) *Attorney, Agent, or Firm* — Duane Morris LLP

(57) ABSTRACT

The present disclosure relates generally to novel methods and compositions for using engineered reprogramming factor(s) for the creation of induced pluripotent stem cells (iPSCs) through a kinetically controlled process. Specifically, this disclosure relates to establishing combinations of reprogramming factors, including fusions between conventional reprogramming factors with transactivation domains, optimized for reprogramming various types of cells. More specifically, the exemplary methods disclosed herein can be used for creating induced pluripotent stem cells from various mammalian cell types, including human fibroblasts. Exemplary methods of feeder-free derivation of human induced pluripotent stem cells using synthetic messenger RNA are also disclosed.

20 Claims, 13 Drawing Sheets
Specification includes a Sequence Listing.

(56) References Cited

OTHER PUBLICATIONS

Hirai et al., "Efficient iPS Cell Production with the MyoD Transactivation Domain in Serum-Free Culture," PLoS One, Mar. 30, 2012, 7(3):1-9.

Lamba et al., "Generation, Purification and Transplantation of Photoreceptors Derived from Human Induced Pluripotent Stem Cells," PLoS One, 2010, 5(1):e8763, 9 pages.

Lee et al., "Dual Mechanisms for Repression of the Monomeric Orphan Receptor Liver Receptor Homologous Protein-1 by the Orphan Small Heterodimer Partner," The Journal of Biological Chemistry, Jan. 25, 2002, 277(4):2463-2467.

Song et al., "Efficient generation of hepatocyte-like cells from human induced pluripotent stem cells," Cell Research, 2009, 19(11):1233-1242.

Wang et al., "Rapid and efficient reprogramming of somatic cells to induced pluripotent stem cells by retinoic acid receptor gamma and liver receptor homolog 1," PNAS, Nov. 8, 2011, 108(45):18283-18288.

Wang et al., "Reprogramming of mouse and human somatic cells by high-performance engineered factors," EMBO Reports, 2011, 12(4):373-378.

Warren et al., "Feeder-Free Derivation of Human Induced Pluripotent Stem Cells with Messenger RNA," Scientific Reports, Sep. 14, 2012, 2:1-7.

International Search Report and Written Opinion dated Oct. 4, 2013, from corresponding International Patent Application No. PCT/US2013/040814, 10 pages.

Rosa, Allesandro et al., Synthetic mRNAs: Powerful Tools for Reprogramming and Differentiation of Human Cells, Cell Stem Cell, Nov. 5, 2010, vol. 7, No. 5, p. 549-550.

Second Office Action in Chinese Patent Application No. 201380025010.4, dated Nov. 18, 2016, in 10 pages.

Search Report in Singapore Application No. 11201509368P, dated Nov. 1, 2016, in 2 pages.

Yakubov, Eduard, "Reprogramming of human fibroblasts to pluripotent stem cells using mRNA of four transcription factors", Biochemical and Biophysical Research Communications, 2010, pp. 189-193, vol. 394.

First Office Action in Japanese Patent Application No. 2015-511803, dated Apr. 10, 2017, in 7 pages.

Hirai, H., et al., "Radical Acceleration of Nuclear Reprogramming by Chromatin Remodeling with the Transactivation Domain of MyoD," Stem Cells, Sep. 2011, vol. 29, No. 9, pp. 1349-1361.

Liew, C-G., "Generation of insulin-producing cells from pluripotent stem cells: from the selection of cell sources to the optimization of protocols", The Review of Diabetic Studies, 2010, vol. 7, No. 2, pp. 82-92.

* cited by examiner

A

B

FEEDER-FREE DERIVATION OF HUMAN-INDUCED PLURIPOTENT STEM CELLS WITH SYNTHETIC MESSENGER RNA

RELATED APPLICATION

This application claims the benefit of, and is a continuation-in-part of, U.S. application Ser. No. 13/893,166, filed on May 13, 2013; which claims the benefit of priority of U.S. provisional application Ser. No. 61/646,292, filed on May 13, 2012. The contents of each of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 7, 2014, is named F6035-00021_SL.txt and is 1,054 bytes in size.

FIELD OF THE INVENTION

The present disclosure relates generally to novel methods and compositions for using engineered reprogramming factor(s) for the creation of induced pluripotent stem cells (iPSCs) through a controlled process. Specifically, this disclosure relates to establishing combinations of reprogramming factors, including fusions between conventional reprogramming factors with transactivation domains, optimized for reprogramming of various cell types. More specifically, the exemplary methods disclosed herein can be used for creating induced pluripotent stem cells from various mammalian cell types, including non-human primate cells. Exemplary methods of feeder-free derivation of human induced pluripotent stem cells using synthetic messenger RNA are also disclosed.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

The therapeutic potential of induced pluripotent stem cells (iPSCs) has spurred efforts to develop reprogramming methods that sidestep the need to genetically modify somatic cells to effect reprogramming to the pluripotent state. The first "non-integrating" approaches to achieve success in this regard—protein transduction, plasmid transfection and the use of adenoviral vectors—were limited in application due to the low efficiencies of iPSC conversion attained. More recently, techniques employing episomal DNA, Sendai virus, and synthetic messenger RNA (mRNA) have been shown to generate "footprint-free" iPSCs with efficiencies comparable to or surpassing those attained using integrating viral vectors. RNA transfection is in principle the most attractive of these methods as it affords precise control over the reprogramming factor (RF) expression time course, while completely obviating any requirement for "clean up" of the reprogrammed cells to purge residual traces of the vector. Current protocols for mRNA-based reprogramming are relatively labor-intensive, however, owing to the need to retransfect daily for the ~2 weeks required for the induction of pluripotency in human cells. These procedures also rely on the use of feeder cells, adding complexity and technical variability to the process while introducing a potential source of contamination with non-human-derived ("xeno") biological material.

A major difficulty of producing induced pluripotent stem cells (iPSCs) has been the low efficiency of reprogramming differentiated•cells into pluripotent cells. Previously, it has been reported that 5% of mouse embryonic fibroblasts (MEFs) were reprogrammed into iPSCs when they were transduced with a fusion gene composed of Oct4 and the transactivation domain of MyoD (called $M_3O$), along with Sox2, Klf4 and c-Myc (SKM). In addition, $M_3O$ facilitated chromatin remodeling of pluripotency genes in the majority of transduced MEFs, including cells that did not become iPSCs. These observations suggested the possibility that more than 5% of cells had acquired the ability to become iPSCs given more favorable culture conditions.

SUMMARY OF THE INVENTION

Successful reprogramming of cells from non-human origins using mRNAs has been elusive due to potential cellular immune responses induced by RNA molecules once they are transfected into cells, particularly mammalian cells. In reprogramming human fibroblast cells, a common practice is to use a viral protein as a decoy receptor to blunt the interferons induced by the transfected mRNA molecules. However, such a strategy of using decoy receptor or other similar strategies have not been successful in reprogramming of fibroblasts from non-human species, including baboons, horses, and dogs.

Accordingly, to address these deficiencies, the present disclosure provides methods and compositions for generating stem cells capable of producing all the different tissues of the body. In certain aspects, using messenger RNA molecules and without the need of viral vectors or feeder cells, the methods disclosed herein can be used to reprogram non-human fibroblasts into induced pluripotent stem cells (iPSCs). The use of the exemplary methods and compositions resulted in a surprising and unexpected improved efficiency over previously reported cell reprogramming methodologies and overcame a previously unsolved problem in suppressing cellular immune responses in non-human mammalian cells.

Accordingly, methods, agents and/or compositions useful for accelerating mRNA-mediated reprogramming by improving the reprogramming factors (RF) cocktail, notably through application of engineered variants of conventional reprogramming factors, such as Oct4 (also referred to as Oct3/4), Sox 2, etc., incorporating transactivation domains of known, strong transcription factors, such as VP16 and MyoD, are provided. The methods and compositions disclosed herein results in a feeder-freeprotocol which dramatically reduces the time, cost and effort involved in mRNA-based reprogramming.

In one aspect, the present disclosure provides a method for dedifferentiating or reprogramming somatic cell comprising: a) transfecting the isolated somatic cell with a composition comprising an effective amount of a fusion product between any one or more of a synthetic mRNA reprogramming factor selected from Oct4, Sox2, Klf4, cMyc, Nanog, and Lin28 and a transactivation domains whereby the somatic cell is reprogrammed or de-differentiated.

In one embodiment, a method of claim 1, wherein the composition comprises Oct4 fused to an N-terminal MyoD transactivation domain is provided. In one embodiment, the Oct4 is fused to an N-terminal MyoD transactivation domain in tandem triplicates.

In one aspect, a method for reprogramming mammalian cells by using any one or more of the synthetic mRNA of reprogramming factor of claim 1, said method compromising: a) growing target cells at a density of 15 k to 500 k cells/well of a standard 6-well plate in a feeder-free surface; b) transfecting cells with varying doses of 50 ng to 800 ng/ml mRNA each time during reprogramming is provided.

In one embodiment, the target cells are grown at a density of 30 k, 75 k, 100 k, or 150 k cells/well of a standard 6-well plate in a feeder-free surface; b) transfecting cells with varying doses of 50 ng to 800 ng/ml mRNA each time during reprogramming, whereas lower doses are used at earlier time points than later time points; c) attaining iPSCs without passaging.

In one embodiment, the target cells are grown at a density of 15 k, 75 k, 100 k, or 150 k cells/well of a standard 6-well plate in a feeder-free surface, whereas the volume of each well is adjusted to be as between 0.5 ml to 5 ml of appropriate medium; transfecting cells with varying doses of 50 ng to 800 ng/ml mRNA each time during reprogramming, whereas lower doses are used at earlier time points than later time points; attaining iPSCs without passaging.

In certain embodiments using lower doses throughout the reprogramming process reduced cellular immune responses and resulted in improved iPSCs success rate. In other embodiments using higher purity mRNA molecules, i.e. without contaminating aberrant transcripts from in vitro transcription allowed cells to be seeded at lower density and survive the repeated transfections and higher iPSCs yield.

In one embodiment, the mammalian cells are human cells. In one embodiment, the method is Xeno-free. In one embodiment, the mammalian cells are non-human primate cells. In one embodiment, the non-human primate cells are cynomolgus monkey cells.

In one embodiment, the one or more factors are selected from the group consisting of mRNAs, regulatory RNAs, siRNA miRNA, and combinations thereof.

In one embodiment, the somatic cells are transfected with at least two different RNAs. In one embodiment, the somatic cells are selected from the group consisting of unipotent, multipotent, pluripotent, and differentiated cells. In one embodiment, the one or more RNAs induces de-differentiation of the somatic cells to unipotent, multipotent, or pluripotent cells.

In one embodiment, the at least one of the factors is selected from the group consisting of OCT4, SOX2, NANOG, LIN28, KLF4 and MYC mRNA. In one embodiment, the OCT4, SOX2, NANOG, and LIN28 mRNA are administered in combination. In one embodiment, the OCT4, SOX2, KLF4 and MYC mRNA are administered in combination.

In one embodiment, the transfected cells are maintained in culture as induced pluripotent stem (iPS) cells. In one embodiment, the transfected cells form induced pluripotent stem cells, further comprising inducing the iPS cells to form differentiated cells.

In one aspect, a method for treating or inhibiting one or more symptoms of a disease or disorder in a patient comprising de-differentiating cells in vitro and administering the cells to the patient is provided. In one embodiment, the composition further comprises Rarg and LrH-1 transaction activation domains. In one embodiment, the composition comprises OCT4 fused to a VP16 transactivation domain.

In one embodiment, the disclosure provides iPSCs derived from non-human primate cells which were used to establish disease model systems because they can produce in-integration-free, feeder-free testing environment without other animal products. Thus, the non-human iPSCs described herein are useful for preclinical testing.

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction. Additional embodiments may be disclosed in the Detailed Description below.

(A) Immunofluorescence imaging showing the TRA-1-60$^+$ colony yield from feeder-free derivations on 50K XFF fibroblasts comparing c-Myc and L-Myc-based cocktails and 4-hour and 24-hour transfection regimens. All wells were transfected for 9 days. 4-hour transfection cultures were fixed for staining on day 15 of the experiment, 24-hour transfection cultures on day 11. (B) 10× bright-field imaging of the 400 ng/ml Stemfect well from the same experiment showing near-confluent hESC-like colonies overtaking the culture on day 9 of the derivation. (C) 10× bright-field time course of a marked field in a follow-up trial in which 100K XFFs were again transfected for 9 days using a 400 ng/ml Stemfect regimen, showing epithelialization and subsequent emergence of hESC-like colonies.

Figure 3:
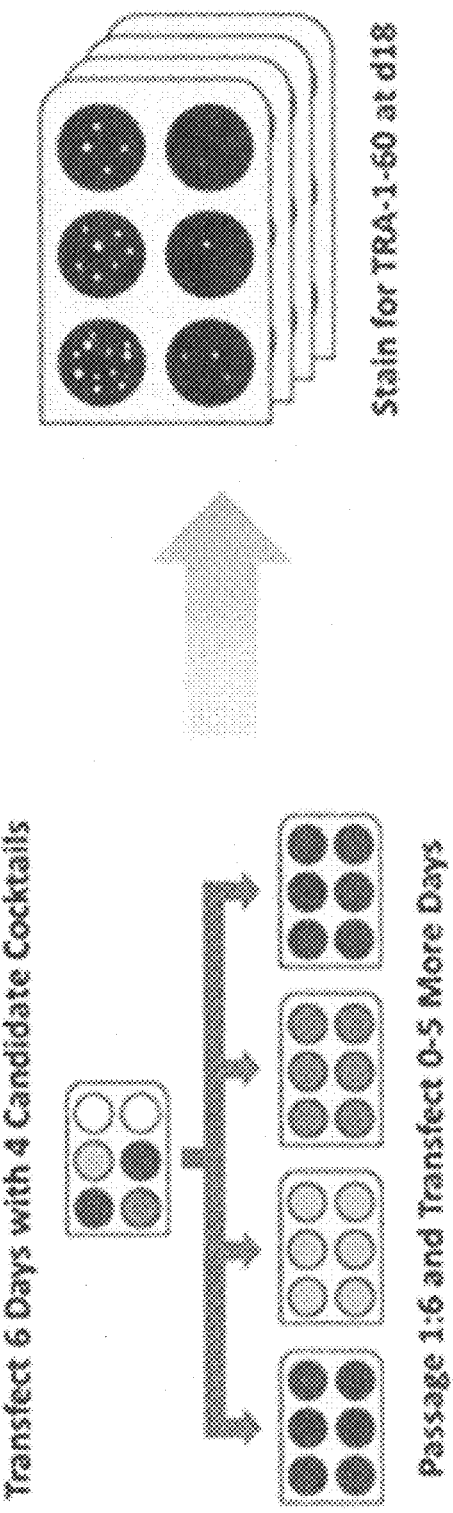

FIG. 3. Comparison of Reprogramming Efficiency Using 4 Different mRNA Cocktails. Flowchart summarizing the four-cocktail comparison experiment.

Figure 4:
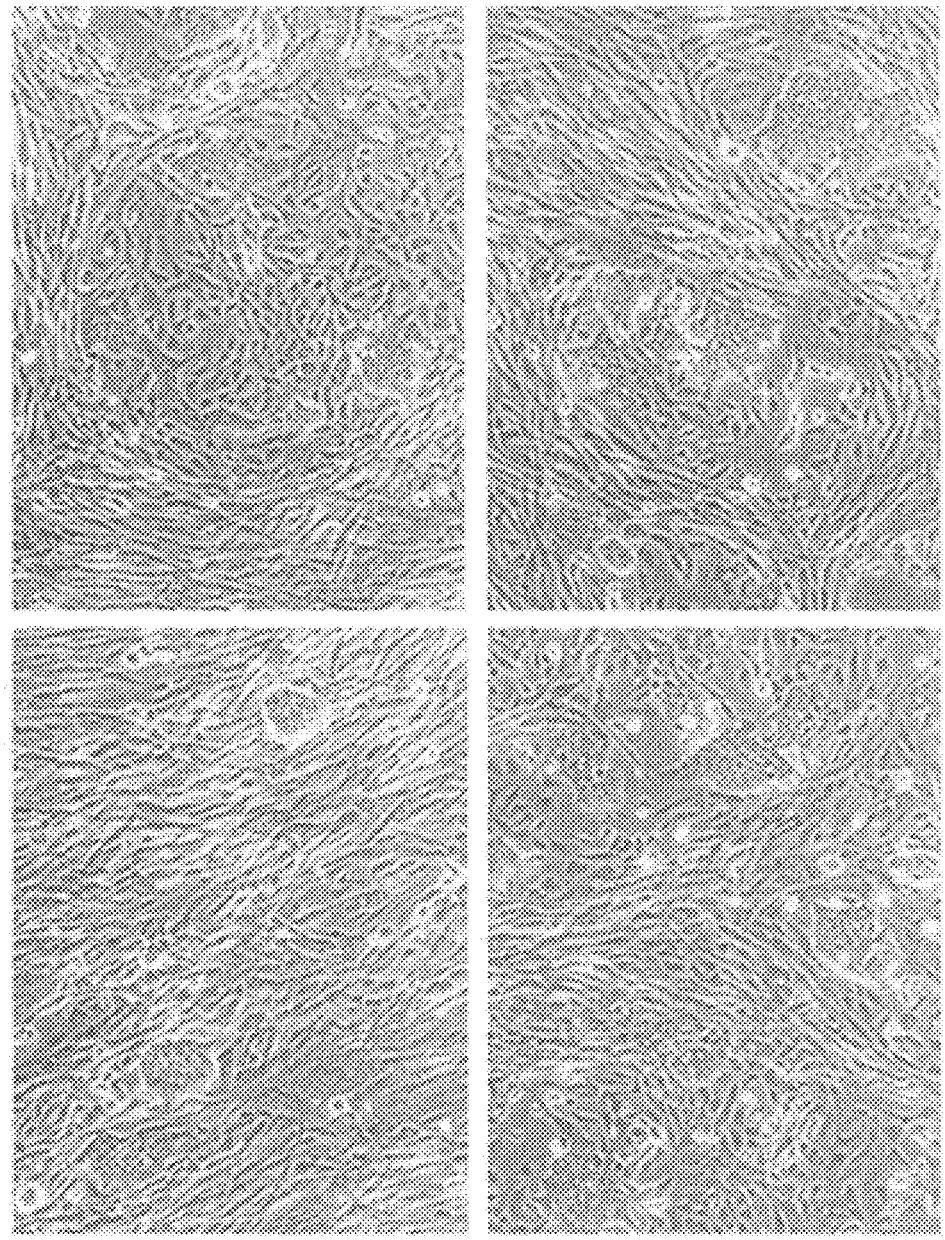

FIG. 4. hESC-Like Colonies in an HDF-a Feeder-Free Reprogramming Culture. 10× bright-field images of emergent hESC-like colonies at day 9 of a feeder-free derivation from 75K HDF-a adult fibroblasts, treated for 9 days with 400 ng/ml mRNA cocktail ($M_3O$+c-Myc$^+$ Nanog$^+$) delivered as a media supplement using Stemfect transfection reagent.

Figure 5:
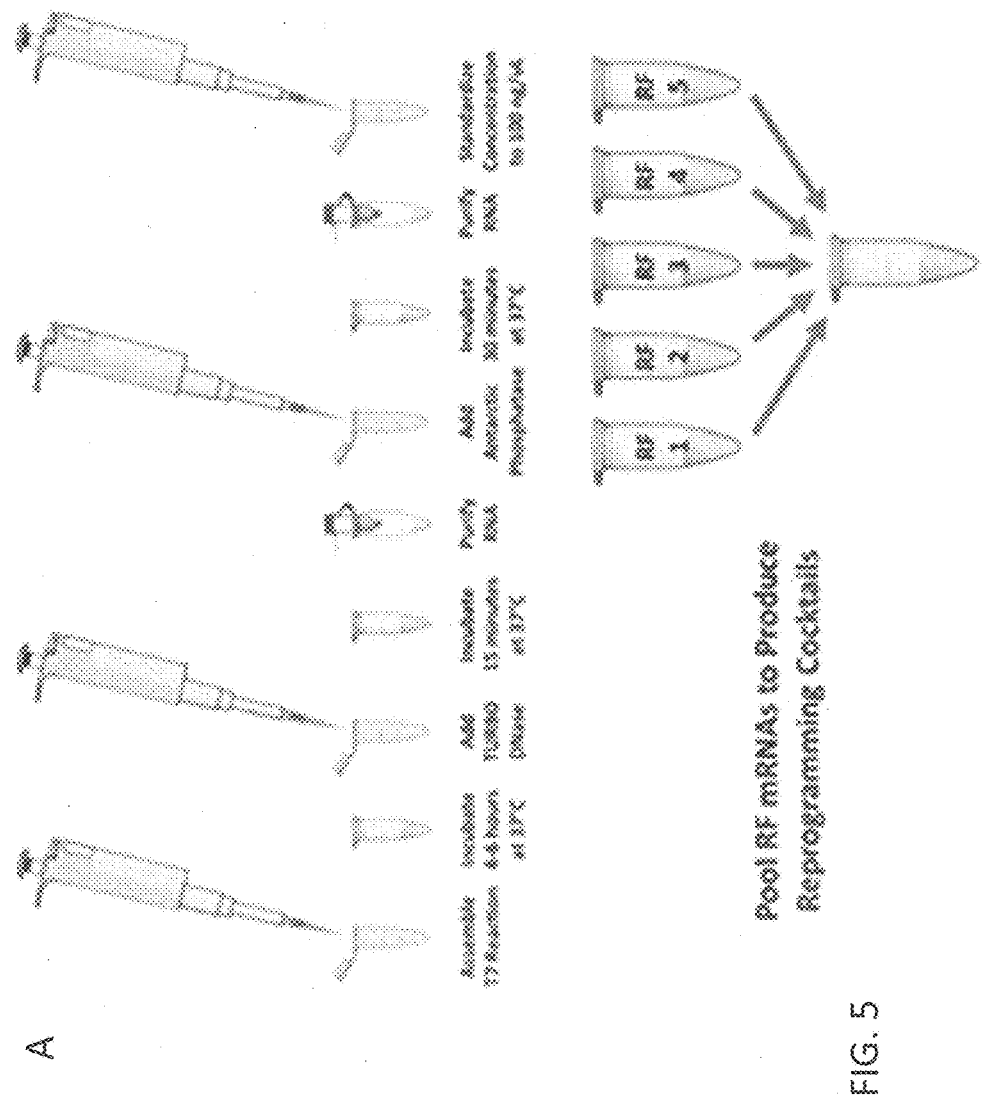
Figure 5:
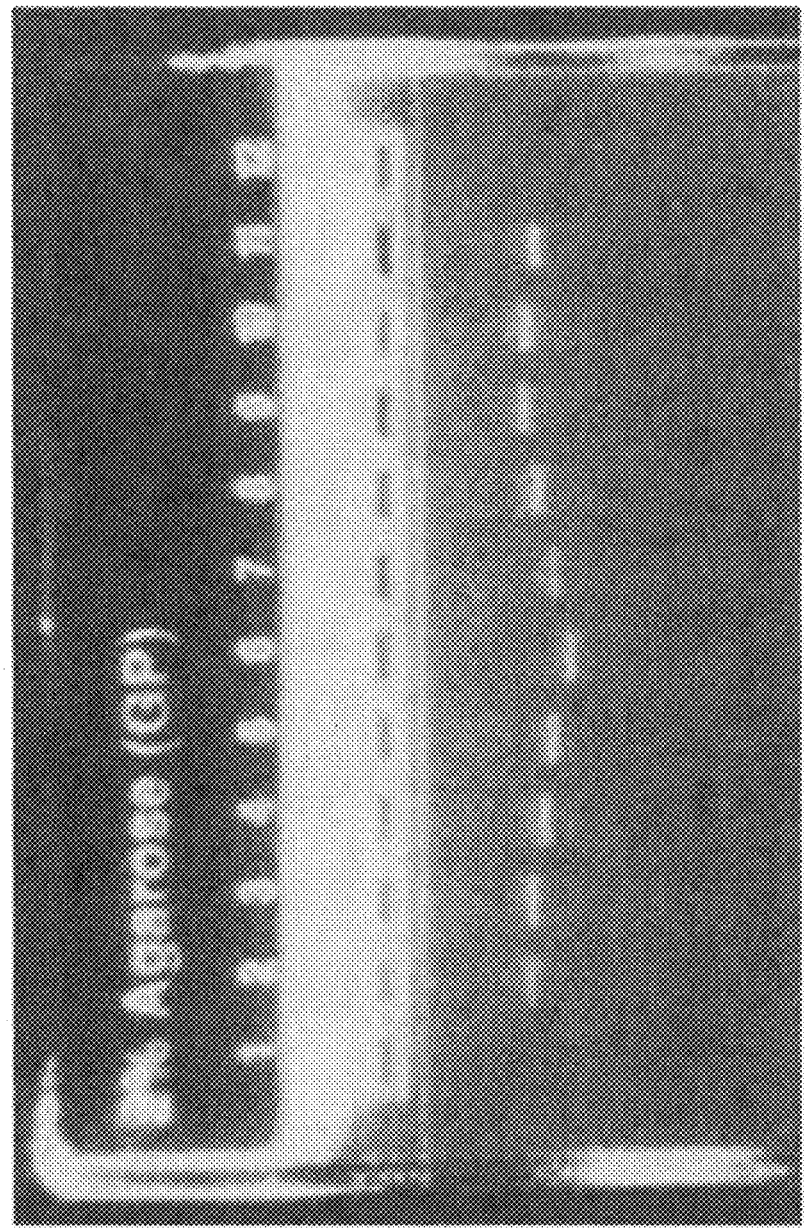

FIG. 5. Generation of Synthetic mRNA Cocktails. (A) Schematic summarizing the procedure for making mRNA reprogramming cocktails. (B) Synthetic mRNAs encoding a number of RFs and fluorescent reporters on a SYBR E-gel. 500 ng of RNA was loaded per lane.

Figure 6:
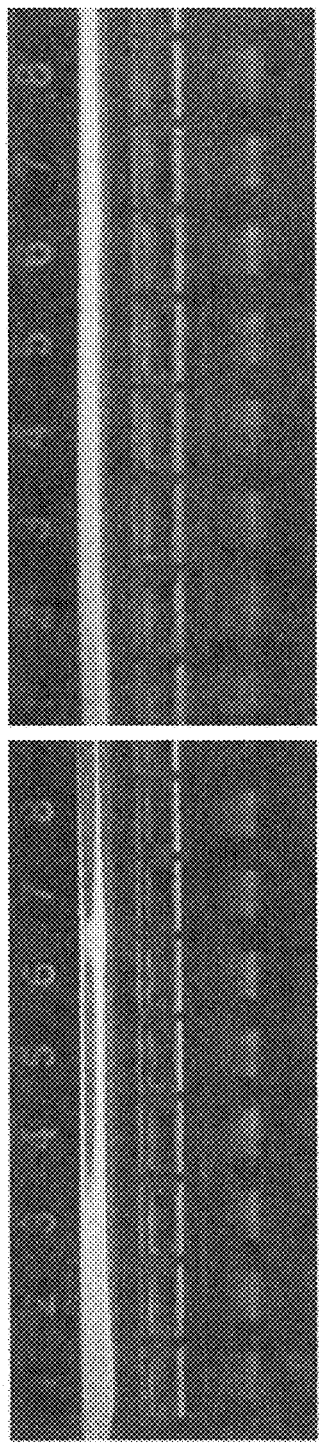

FIG. 6. Generation of synthetic mRNA Cocktails using 2-Thio-Uracil for reprogramming cocktails. Synthetic mRNAs encoding a number of RFs on a SYBR E-gel. The mRNAs have 10% of their Uracil bases replaced by 2-Thio-Uracils. 100 ng of RNA was loaded per lane.

Figure 7:
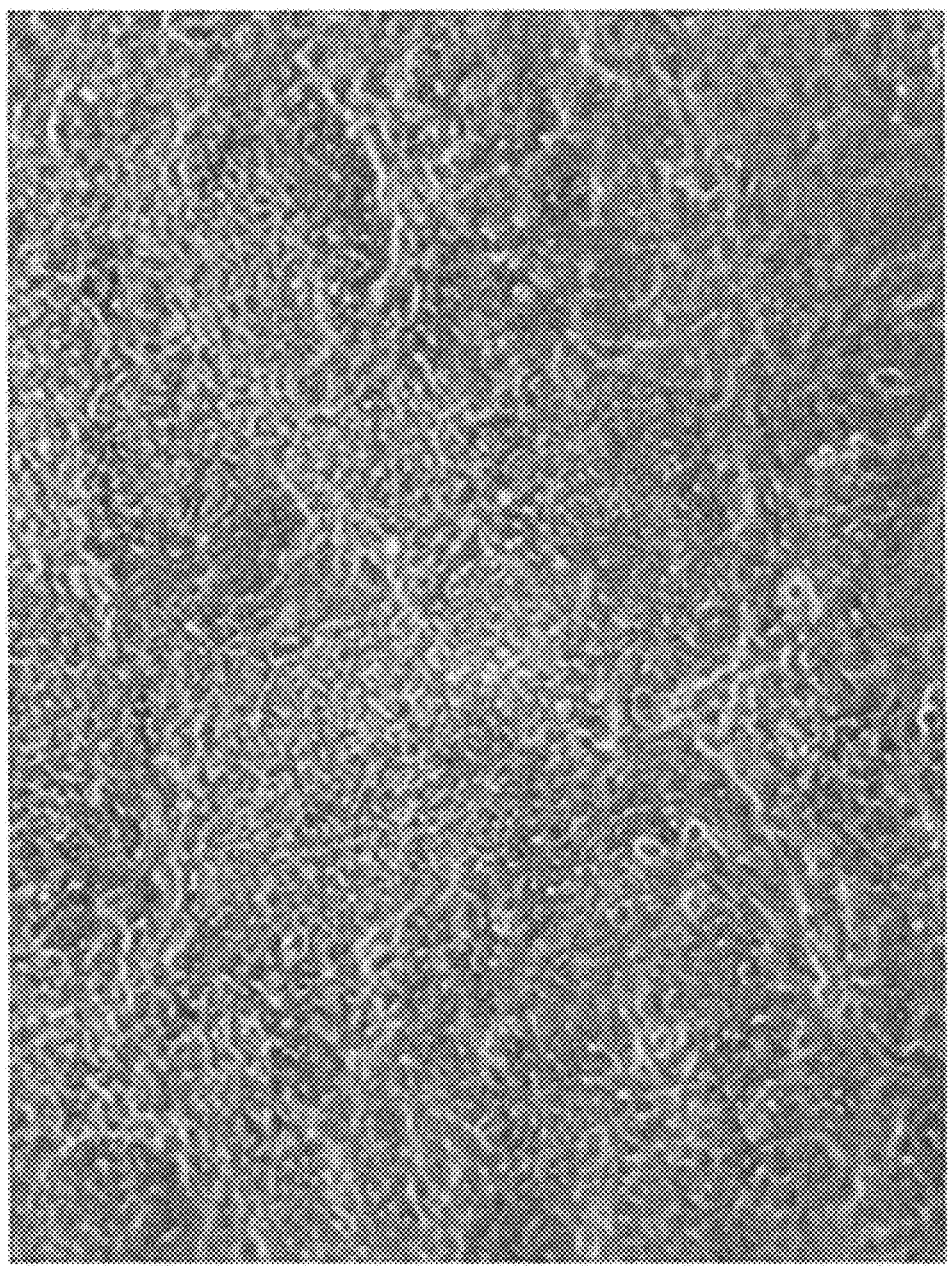
Figure 7:
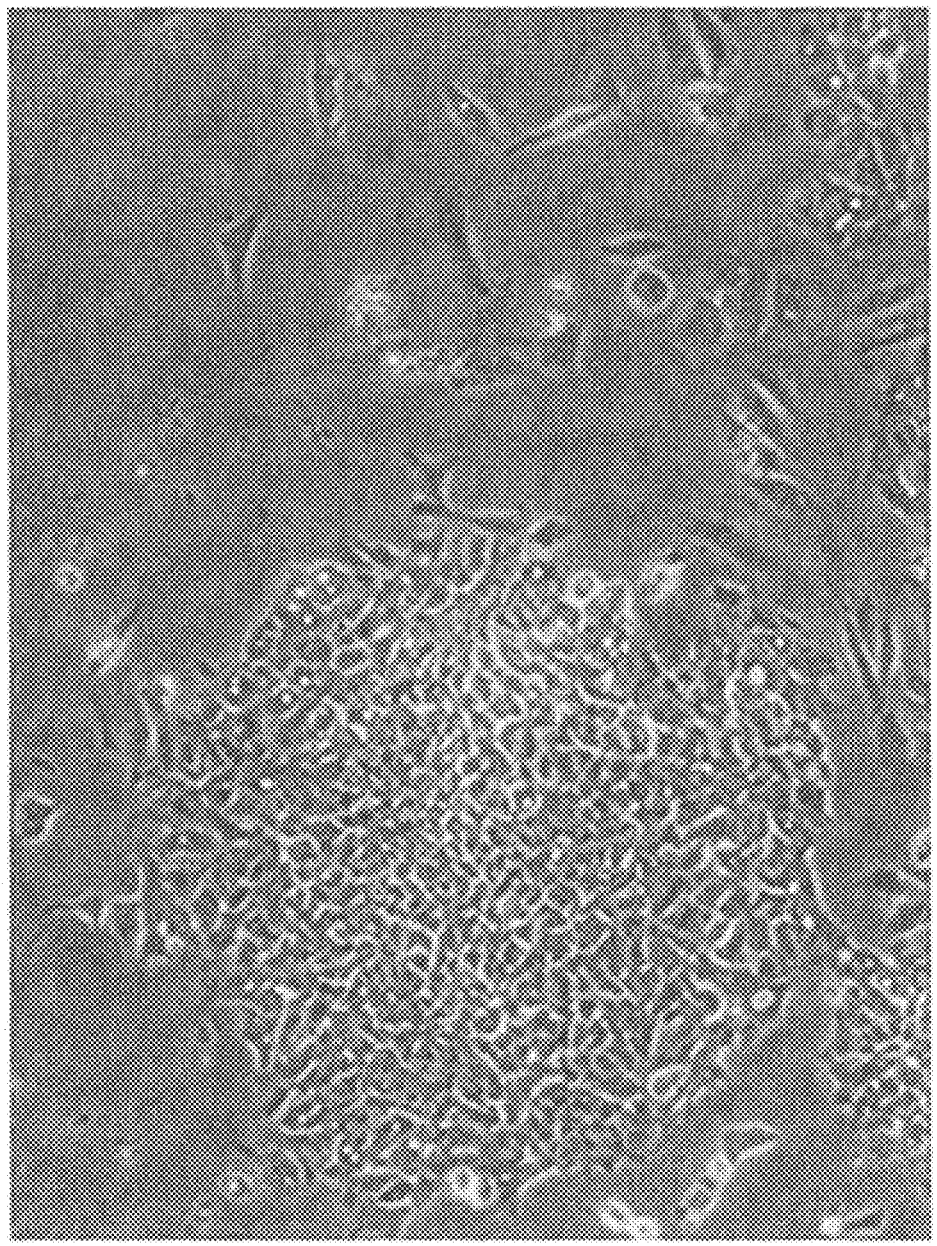

FIG. 7. Human iPSCs created using mRNA cocktails with mRNAs modified with 2-Thio-Uracil. Populations of human iPSCs after (A) 7 days or (B) 11 days of reprogramming during different reprogramming runs in Pluriton (A) or Allele Reprogramming media (B).

Figure 8:
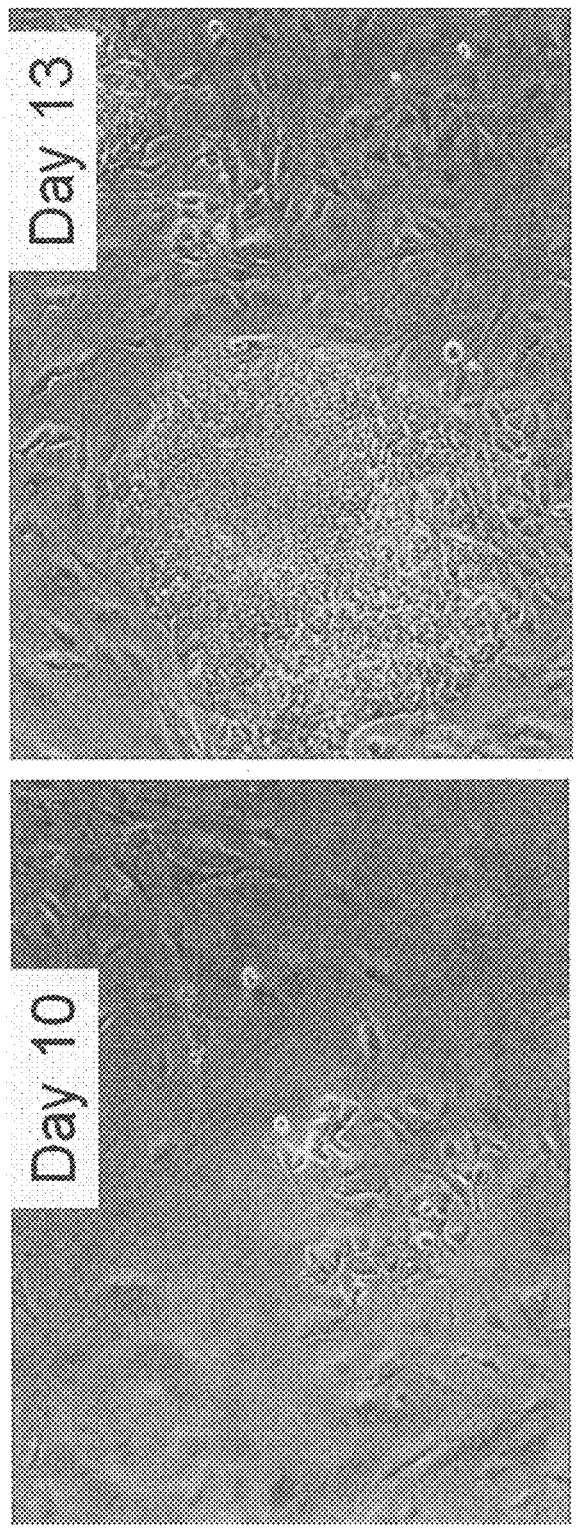

FIG. 8. Cynomolgus Monkey iPSC colonies created using mRNA cocktail in feeder-free reprogramming culture. Shown in the pictures are 10× bright-field images of emergent hESC-like colonies on day 10 and day 13. In the day 10 panel, the cells near the center exhibit morphology changes from fibroblast to stem cells. In the day 13 panel, the cells formed a large colony of fully transformed monkey iPSCs.

DETAILED DESCRIPTION

When describing the present invention, all terms not defined herein have their common meanings recognized in the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention.

Differentiated cells can be reverted to a pluripotent state by the expression of a select group of transcription factors opened up the prospect that patient-specific cells might be used to generate cells of any desired type for the study of genetic disease in vitro and ultimately for cell-replacement therapy. Expression of the reprogramming factors can be achieved through the application of viral vectors which integrate into the genome, and iPSC derivations are still usually performed with integrating retrovirus or lentivirus. The attendant modification of the genome represents an important hurdle to therapeutic application of iPSCs, while the possibility of reactivated expression from integrated viral cassettes is a concern even for in vitro studies. Considerable progress has been made recently in the application of novel expression vectors that alleviate or obviate the genome-modification problem. Lentiviral vectors are now available which encode the multiple factors required for iPSC induction in a single polycistronic cassette flanked by lox recombination sites, which allows for almost-seamless excision of the transgene after reprogramming through transient expression of Cre recombinase. Transgene insertion with subsequent excision can also be effected by using a transposon vector followed by brief expression of transposase. Several different types of non-integrating DNA vector have been employed which can transiently express reprogramming factors for enough time to induce pluripotency, including adenovirus, plasmid and episomal DNA. It has also proved possible to generate iPSC by repeated transduction of cells with recombinant RF proteins incorporating cell-penetrating peptides, albeit with low efficiency. Relatively efficient iPSC conversion can now be achieved using Sendai virus, which has a completely RNA-based reproductive cycle, and by sustained transfection of synthetic mRNA transcripts encoding the Yamanaka factors.

The application of mRNA transfection to reprogramming (and potentially to directed differentiation and transdifferentiation) is appealing as this system allows the expression of reprogramming cocktails and even individual component factors to be modulated on a daily basis simply by changing which transcripts are added to the cell culture media. Once transfection of a particular factor is terminated, ectopic expression within the target cells ceases in short order due to the rapid decay of mRNA in the cytoplasm. In contrast to non-integrating DNA vectors or RNA viruses, no cleanup is required with mRNA transfection, nor is there any risk of random genomic integration or persistent viral infection. These advantages assume greater significance if we envisage that multiple rounds of ectopic RF expression may ultimately be employed to go from a patient biopsy to specialized cells of a desired type via an iPSC intermediate. Nonetheless, there are drawbacks to mRNA-based reprogramming as currently practiced. While the expression of RFs is typically robust for on the order of 24 hours after mRNA is transfected, it takes about two weeks of factor expression to induce pluripotency in human cells, so the hands-on time required to reprogram cells with this technique is relatively high. Not all cell types and culture media are equally conducive to efficient mRNA delivery, and this is currently an impediment to mRNA-based reprogramming of certain cell types of interest, including blood cells. It has also so far proved necessary to employ a feeder layer of mitotically-arrested fibroblasts in order to successfully reprogram cells into iPSCs using the mRNA method. These feeder cells buffer the population density of the culture as the target cells grow out from a low starting density over the extended time course required for iPSC induction, evening out the delivered dose of RNA and transfection reagent (both of which have associated toxicities) and supporting the viability of the target cells in the face of the pro-apoptotic and cytostatic forces engendered by the reprogramming process. This requirement adds complexity and hands-on time to the procedure and introduces an important source of technical variability, especially given that the feeders are themselves subject to transfection. The presence of a feeder layer also impedes monitoring and analysis of the reprogramming process. Finally, although human feeder cells are currently the standard for mRNA reprogramming, even these cells are a potential source of xeno-biological contamination when non-human animal products are used in their derivation and expansion.

Accordingly, in view of the problems associated with the previously known procedure, novel methods, materials, and protocols are provided herein to produce iPSCs with improved efficiency of reprogramming and improved quality of the resultant cells. The current invention embodiments were used successfully to achieve significant surprising and unexpected improvements through potentiation of the RF cocktail delivered to the cells. The current invention embodiments also provide a novel protocol(s) which compresses and streamlines the mRNA reprogramming process, and which support the production of footprint-free iPSCs from human fibroblasts without the use of feeder cells or any other potentially xeno-contaminated reagents. The novel methods and compositions provided herein will extend the benefits of the previously known mRNA method and help clear remaining roadblocks to the therapeutic application of iPSC technology.

The present disclosure relates generally to methods of using engineered reprogramming factor(s) for the creation of induced pluripotent stem cells (iPSCs) through a kinetically controlled process. More specifically, this invention relates to establishing combinations of reprogramming factors, including fusions between conventional reprogramming factors with transactivation domains, optimized for reprogramming different types of cells; introducing these factors as synthetic messenger RNA (mRNA) into cultured mammalian cells at the preferred density by methods that result in appropriate levels of transgene expression; maintaining cell under defined conditions to result in previously unattainable efficiency of reprogramming Compared to other methods that are known in the art, the current invention dramatically reduces the time, cost and effort involved in reprogramming, with the options to be completely feeder-free and Xeno-free, and without passaging. The materials and procedures disclosed herein are useful for creating induced pluripotent stem cells from different types of mammalian cells, including human fibroblasts.

Aspects of the disclosure also provide methods for generating stem cells capable of producing variety of different tissues of the human body by using messenger RNA molecules without the need of viral vectors, animal products or feeder cells. The novel methods disclosed herein can be used to reprogram human fibroblasts into induced pluripotent stem cells (iPSCs) with surprising and unexpected efficiency under optimal conditions.

The present disclosure provides useful processes and compositions for treating non-human mammalian cells (e.g. fibroblasts) with cocktails of "cleaned-up" mRNAs encoding exemplary reprogramming factors described herein, The mRNA composition can be used without causing the treated cells to undergo cell death associated with introduction of the mRNA molecules. In one embodiment, the non-human mammalian cells are cynomolgus monkey cells. In another embodiment, the cynomolgus monkey cells are seeded in a gradient in a well so that cells grow at varying local densities.

Definitions

As used herein, cells suitable for use with the method include, but are not limited to, primary cells and established cell lines, embryonic cells, immune cells, stem cells, and differentiated cells including, but not limited to, cells derived from ectoderm, endoderm, and mesoderm, including fibroblasts, parenchymal cells, hematopoietic cells, and epithelial cells. As used herein, stem cells include unipotent cells, multipotent cells, and pluripotent cells; embryonic stem cells, and adult stem cells such as hematopoietic stem cells, mesenchymal stem cells, epithelial stem cells, and muscle satellite cells. In one embodiment, somatic cells are de-differentiated or reprogrammed. Any suitable somatic cell can be used. Representative somatic cells include fibroblasts, keratinocytes, adipocytes, muscle cells, organ and tissue cells, and various blood cells including, but not limited to, hematopoietic cells including hematopoietic stem cells, and cells that provide short- or long-term hematopoietic engraftment. The most preferred cell types include, but are not limited to, human fibroblasts, keratinocytes and hematopoietic stem cells. The methods are particularly useful for de-differentiating and optionally re-differentiating cells, without permanent alteration of cell genomes.

RNAs useful in the disclosed method include mRNAs, regulatory RNAs, or small RNAs such as siRNA or miRNA wherein the one or more mRNAs encode polypeptides that function to de-differentiate or reprogram the cell. The efficiency of transfection is high. Typically more than 90% of the transfected cell population will express the introduced RNA. Therefore, it is possible to transfect cells with one or more distinct RNAs. For example, the population of cells can be transfected with one or more distinct mRNAs, one or more distinct siRNAs, one or more distinct miRNAs, or combinations thereof. The population of cells can be transfected with multiple RNAs simultaneously in a single administration, or multiple administrations can be staggered minutes, hours, days, or weeks apart. Transfection of multiple distinct RNAs may be staggered. For example, if it is desirable for a first RNA to be expressed prior to expression of one or more additional RNAs.

The level of expression of the transfected RNA can be manipulated over a wide range by changing the amount of input RNA, making it possible to individually regulate the expression level of each transfected RNA. The effective amount of input RNA is determined based on the desired result. Furthermore, the PCR-based technique of mRNA production facilitates the design of mRNAs with different structures and domain combinations. RNAs useful in the disclosed methods are known in the art, and will be selected based on the target host cell type as well as the pathway or cellular activity to be manipulated, or the therapeutic application. Constructs useful for de-differentiating cells, for example, converting adult, differentiated somatic cells into stem cells, can be constructed based on known genes, mRNAs, or other nucleotide or protein sequences.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences.

A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

Exemplary genomic, mRNA (cDNA), and protein sequences for OCT4 are known in the art, see, for example, (OCT4) POU5F1 POU class 5 homeobox [*Homo sapiens*] Gene ID: 5460, which provides mRNA (cDNA) sequences Genbank accession no. NM_001173531.1 entitled *Homo sapiens* POU class 5 homeobox 1 (POU5F1), transcript variant 3, mRNA; Genbank accession no. NM_002701.4 entitled *Homo sapiens* POU class 5 homeobox 1 (POU5F1) transcript variant 1, mRNA; and Genbank accession no. NM_203289.4 entitled *Homo sapiens* POU class 5 homeobox 1 (POU5F1), transcript variant 2, mRNA. Exemplary genomic, mRNA (cDNA), and protein sequences for SOX2 are also known in the art, see, for example, SOX2 SRY (sex determining region Y)-box 2 [*Homo sapiens*], *Gene ID:* 6657, which provides mRNA (cDNA) sequence Genbank Accession no. NM_003106.2 entitled mRNA sequence *Homo sapiens* SRY (sex determining region Y)-box 2 (SOX2), mRNA. Exemplary genomic, mRNA (cDNA), and protein sequences for NANOG are also known in the art, see for example NANOG Nanog homeobox [*Homo sapiens*], Gene ID: 79923, which provides the mRNA (cDNA) sequence Genbank accession no. NM_024865.2 entitled *Homo sapiens* Nanog homeobox (NANOG), mRNA. Exemplary genomic, mRNA (cDNA), and protein sequences for LIN28 are also known in the art, see for example LIN28A homolog A (*C. elegans*) [*Homo sapiens*], Gene ID: 79727, which provides the mRNA (cDNA) sequence Genbank accession no. NM_024674.4 entitled *Homo sapiens* lin-28 homolog A (*C. elegans*) (LIN28A), mRNA. Exemplary genomic, mRNA (cDNA), and protein sequences for KLF4 are known in the art, see, for example, KLF4 Kruppel-like factor 4 (gut) [*Homo sapiens*], Gene ID: 9314, which provides the mRNA (cDNA) sequence Genbank accession no. NM_004235.4 entitled *Homo sapiens* Kruppel-like factor 4 (gut) (KLF4), mRNA. mRNA sequences for MYC are also known in the art, see for example MYC v-myc myelocytomatosis viral oncogene homolog (avian) [*Homo sapiens*], Gene ID: 4609, which provides the mRNA (cDNA) sequence Genbank accession no. NM_002467.4 entitled *Homo sapiens* v-myc myelocytomatosis viral oncogene homolog (avian) (MYC), mRNA.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

As used herein, the term "stem cell" refers to an undifferentiated cell that can be induced to proliferate. The stem cell is capable of self-maintenance, meaning that with each cell division, one daughter cell will also be a stem cell. Stem cells can be obtained from embryonic, fetal, post-natal, juvenile or adult tissue. The term "progenitor cell", as used herein, refers to an undifferentiated cell derived from a stem cell, and is not itself a stem cell. Some progenitor cells can produce progeny that are capable of differentiating into more than one cell type.

The term "induced pluripotent stem cell" (or "iPScell"), as used herein, refers to a stem cell induced from a somatic cell, e.g., a differentiated somatic cell, and that has a higher potency than said somatic cell. iPS cells are capable of self-renewal and differentiation into mature cells, e.g., smooth muscle cells. iPS may also be capable of differentiation into smooth muscle progenitor cells.

As used herein the term "isolated" with reference to a cell, refers to a cell that is in an environment different from that in which the cell naturally occurs, e.g., where the cell naturally occurs in a multicellular organism, and the cell is removed from the multicellular organism, the cell is "isolated." An isolated genetically modified host cell can be present in a mixed population of genetically modified host cells, or in a mixed population comprising genetically modified host cells and host cells that are not genetically modified. For example, an isolated genetically modified host cell can be present in a mixed population of genetically modified host cells in vitro, or in a mixed in vitro population comprising genetically modified host cells and host cells that are not genetically modified.

A "host cell," as used herein, denotes an in vivo or in vitro cell (e.g., a eukaryotic cell cultured as a unicellular entity), which eukaryotic cell can be, or has been, used as recipients for a nucleic acid (e.g., an exogenous nucleic acid), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation.

The term "genetic modification" and refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein, the term "exogenous nucleic acid" refers to a nucleic acid that is not normally or naturally found in and/or produced by a cell in nature, and/or that is introduced into the cell (e.g., by electroporation, transfection, infection, lipofection, or any other means of introducing a nucleic acid into a cell).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease.

"Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, a human, a non-human primate, a rodent (e.g., a mouse, a rat, etc.), an ungulate, a canine, a lagomorph, a feline, etc. In some embodiments, a subject of interest is a human. In some embodiments, a subject is a non-human animal such as a monkey, rodent, or a lagomorph.

A "therapeutically effective amount" or "efficacious amount" means the amount of a compound, a nucleic acid, or a number of cells that, when administered to a subject for treating a disease, is sufficient to effect such treatment for the disease. The "therapeutically effective amount" will vary depending on the compound or the cell, the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

In one aspect of the current disclosure, mRNA-based reprogramming could be enhanced through the use of engineered variants of Oct4 or Sox 2 incorporating an N-terminal MyoD transactivation domain (Hirai et al, Stem Cells, 2011) or a C-terminal triple repeat of the VP16 transactivation domain (Wang et al, EMBO Reports, 2011; in which synthetic reprogramming factors were prepared by fusing the VP16 transactivation domain to OCT4 (also known as Pou5f1), NANOG and SOX2, respectively, these synthetic factors could reprogram both mouse and human fibroblasts with enhanced efficiency and accelerated kinetics), or by augmenting the "standard" RF cocktail with two additional factors, Rarg and Lrh-1 (Wang et al, PNAS, 2011). The contents of each of which are hereby incorporated in reference. Strong transcription activators can effectively recruit multiple chromatin remodeling complexes when binding to DNA at specific sites. A good example is MyoD, a master transcription factor for skeletal myogenesis that can switch the fate of differentiated cells. Hirai et al. speculated that since MyoD is such a strong transcription factor, it can increase chromatin accessibility to iPS factors if fused together. When mouse or human cells are transduced with retroviral vectors carrying an Oct-MyoD TAD fusion gene, together with Sox2 and Klf4, they increased the number of iPSC colonies by ~50-fold compared to canonical iPS factors. Similarly, VP16, widely known for its being a robust transcription activator, can exhibit strong stimulation effects on reprogramming when fused to different iPS factors.

Exemplary Preparation of Human iPSCs

The method can also be widely used for re-differentiating or reprogramming of cells, for example, to produce iPS cells that can be further modulated to form hematopoietic stem cells, mesenchymal stem cells, epithelial stem cells, and muscle satellite cells, or differentiated cells of human tissues, including, but not limited to, red blood cells, white blood cells including lymphocytes, platelets, stromal cells, fat cells, bone cells including osteoclasts, epithelial tissue including skin cells, muscle tissue including smooth muscle, skeletal muscle, and cardiac muscle, vascular tissue including endothelial cells, liver tissue including hepatocytes, and nervous tissue including neurons. Methods of inducing differentiation of iPS cells into various differentiated cells types, including, but not limited to, cardiomyocytes, hematopoietic stem cells, bone cells such as, osteoclasts, hepatocytes, retinal cells, and neurons, stem cells including, but not limited to, isolated embryonic stem cells, hematopoietic stem cells, and induced pluripotent stem cells can be induced to differentiate by transient transfection with RNAs that induce differentiation. Additionally, or alternatively, cells can be re-differentiated by culturing the cells under cell type-specific conditions. For example, iPS cells can be maintained on CF-1 feeders and subsequently adapted to feeder-free conditions. iPS cells can be induced to form differentiated retinal cells by culturing the cells in the presences of noggin, Dkk-1, and IGF-1

Figure 1:
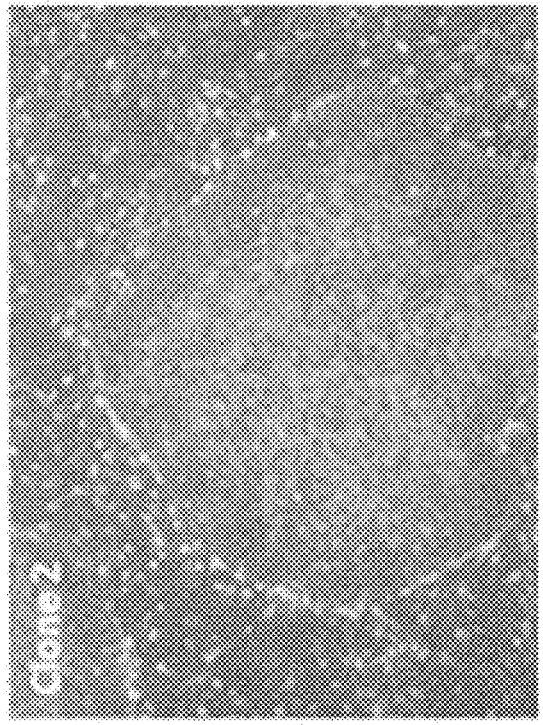
FIG. 1. iPSC Colonies Derived with $M_3O$-Based mRNA Reprogramming Cocktail. (A) 10× bright-field images of two of the expanded iPSC clones derived from the first $M_3O$-based BJ reprogramming trial. (B) Immunostaining of expanded clones for pluripotency markers.
Figure 1:
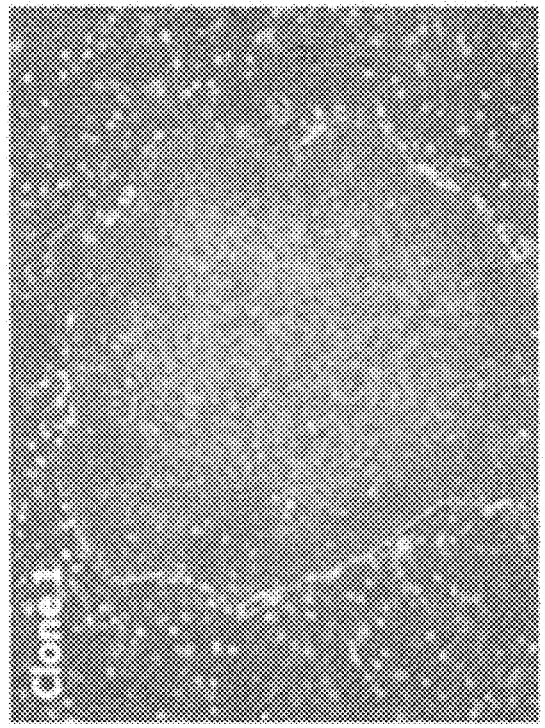
Figure 1:
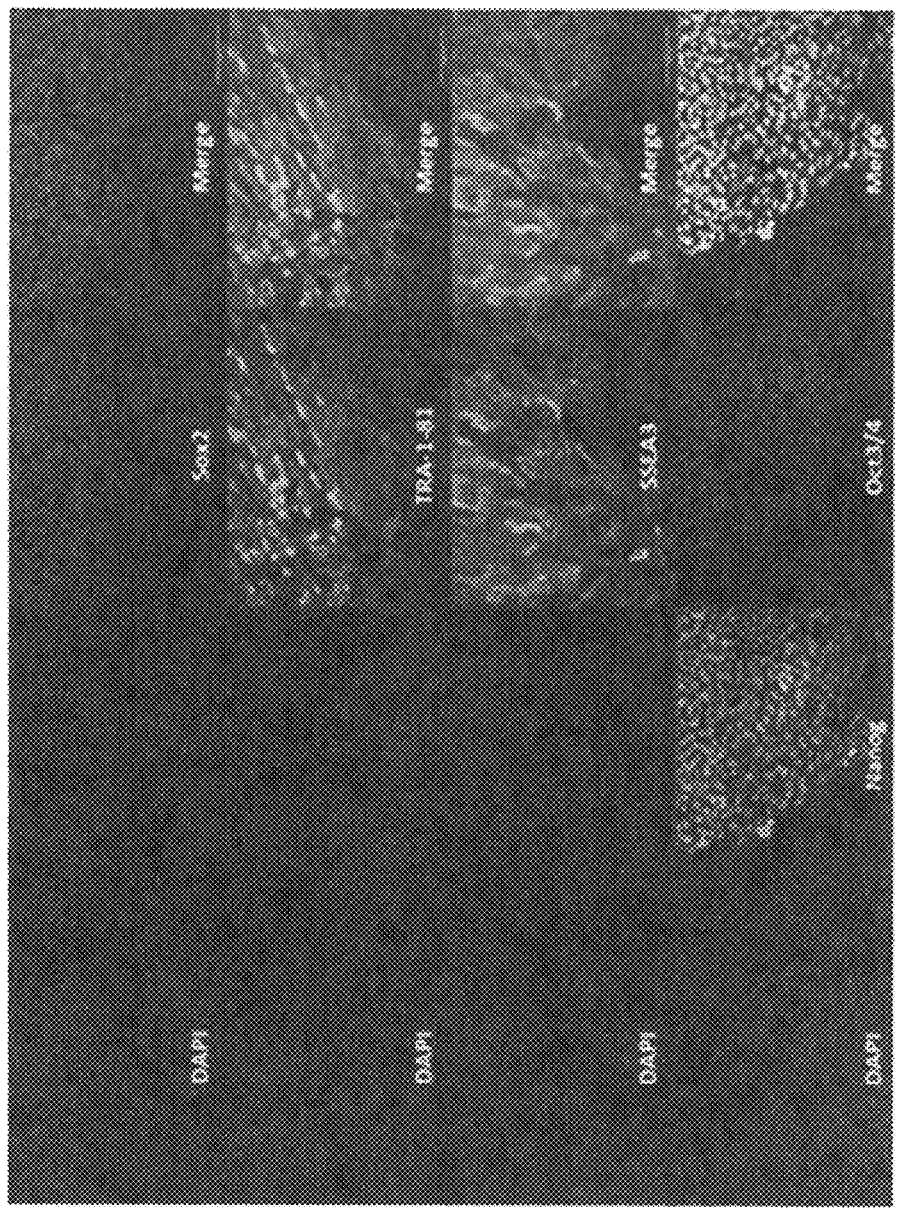

Previously reported methodologies relied on integrating vectors, i.e. viruses or plasmids, to carry the modified factors. In one embodiment, a reprogramming trial was performed comparing the performance of six different mRNA combination cocktails comprising transcripts for five factors for mRNA reprogramming (Oct4, Sox2, Klf4, cMyc-T58A and Lin28), or a 7-reprogram factor RF cocktail including Rarg and Lrh-1, each combination was tested in three variations based on wild-type Oct4 and the MyoD- and VP16-Oct4 fusion constructs (designated $M_3O$ and VPx3, respectively). BJ fibroblasts were transfected in feeder-based reprogramming cultures for 11 days, by which time advanced morphologies were apparent in several of the wells. Over the next few days, colonies with characteristic hESC morphologies emerged in wells transfected with the cocktails based on wild-type Oct4 and $M_3O$. The target cells in the VPx3-transfected cultures retained a fibroblastic morphology, albeit while showing accelerated growth and some tendency to aggregate into foci, and no colonies emerged. The 5-factor and 7-factor embodiments of the wild type Oct4 and $M_3O$-based cocktails showed similar colony productivity, hence no advantage accrued from the inclusion of Rarg and Lrh-1 in the cocktails. However, the $M_3O$ cocktail gave several times the number of colonies produced with wild-type Oct4. In light of this result, colonies were picked from the $M_3O$ 5-factor well for expansion and further analysis (FIG. 1). Pluripotency of $M_3O$-derived colonies was confirmed by immunostaining for nuclear and cell-surface markers, and by in vitro differentiation into the three primary germ layers. Six expanded iPSC clones were subjected to karyotype analysis and DNA fingerprinting, the cells' karyotypic normality and BJ lineage being confirmed in all cases.

The method can also be widely used for re-differentiating or reprogramming of cells, for example, to produce iPS cells that can be further modulated to form hematopoietic stem cells, mesenchymal stem cells, epithelial stem cells, and muscle satellite cells, or differentiated cells of human tissues, including, but not limited to, red blood cells, white blood cells including lymphocytes, platelets, stromal cells, fat cells, bone cells including osteoclasts, epithelial tissue including skin cells, muscle tissue including smooth muscle, skeletal muscle, and cardiac muscle, vascular tissue including endothelial cells, liver tissue including hepatocytes, and nervous tissue including neurons. Methods of inducing differentiation of iPS cells into various differentiated cells types, including, but not limited to, cardiomyocytes, hematopoietic stem cells, bone cells such as, osteoclasts, hepatocytes, retinal cells, and neurons, are known in the art (Song at al., *Cell Res.,* 19(11):1233-42 (2009), Lamba et al., *PLoS One,* 5(1):e8763 (2010), Gai et al., *Cell Biol Int.* 200933(11):1184-93 (2009). Grigoriadis et al., *Blood,* 115 (14):2769-76 (2010)). Stem cells including, but not limited to, isolated embryonic stem cells, hematopoietic stem cells, and induced pluripotent stem cells can be induced to differentiate by transient transfection with RNAs that induce differentiation. Additionally, or alternatively, cells can be re-differentiated by culturing the cells under cell type-specific conditions. For example, iPS cells can be maintained on CF-1 feeders and subsequently adapted to feeder-free conditions. iPS cells can be induced to form differentiated retinal cells by culturing the cells in the presences of noggin, Dkk-1, and IGF-1 In another aspect, the potency of the mRNA cocktail could be further enhanced by the inclusion of Nanog transcripts. In this embodiment, four wells containing 50K BJ fibroblasts on feeders were transfected with wild-type Oct4 or $M_3O$-based 5-factor or 6-factor cocktails for six days, and each culture was then passaged 1:6 onto fresh feeders to populate a 6-well plate (4). Transfection was continued for 0-5 more days within each plate. The cultures were fixed and stained with TRA-1-60 antibodies on day 18 (where day 0 corresponds to the first transfection) in order to assess the impact of the different cocktails and transfection time courses on iPSC productivity. The results showed that adding Nanog to the cocktail was highly beneficial regardless of the Oct4 variant employed, while the greatest conversion efficiency was attained when $M_3O$ and Nanog were used together.

In one embodiment, the efficacy of the $M_3O$-based 5-factor or 6-factor cocktails was confirmed in additional feeder-based experiments using three additional human fibroblast lines (HDF-f, HDF-n and XFF). Reprogramming kinetics and efficiency were markedly improved with all three of these low-passage lines, which displayed faster native population doubling times than BJs in normal expansion culture. In some cases, we obtained hESC-like colonies from as little as six days of transfection, although the yields were much higher in experiments where transfection was continued for a few more days. Experiments involving periodic reinforcement of the feeder layer by addition of fresh cells suggested that while this strategy might give some benefits, they would be offset by the complexity of the resulting protocol. We therefore decided to focus on applying the more potent cocktails to development of a streamlined, feeder-free protocol.

The current disclosure relates to creation of feeder-free iPSCs. Feeder-independent iPSC derivation has generally proved somewhat challenging regardless of the reprogramming technology employed, but raises special difficulties in the context of a sustained transfection regime. There is a lower limit to the density at which fibroblasts can be plated without compromising cell viability and proliferative activity. The propensity of cells to undergo mitotic arrest or apoptosis in sparse cultures is exacerbated when the cells are stressed by transfection and by ectopic expression of reprogramming factors. Moreover, RNA doses which are well tolerated at the high cell densities characteristic of feeder-based reprogramming produce more severe cytotoxic effects when distributed among fewer cells. At the same time, the penetrance of expression which can be achieved with mRNA transfection declines sharply after fibroblasts reach confluence, perhaps owing to a down-regulation of endocytosis associated with contact inhibition and G1 arrest. This reduced permissiveness to transfection in crowded cultures seems to be alleviated during reprogramming after cells undergo mesenchymal-to-epithelial transition (MET). However, the ~7 days typically required for human fibroblasts to reach MET when using current mRNA cocktails makes it hard to head off the problem of fibroblastic overgrowth even if cells are plated at the lowest survivable initial densities. Cells can be thinned by passaging to postpone this fate, but the plating efficiency of highly stressed reprogramming intermediates is hard to predict and, in any case, a passaging-based derivation protocol would sacrifice convenience and scale poorly to high-throughput applications. In certain embodiments, cells can also be seeded at a gradient in a well so that different local cell density can facilitate the repeated transfection, The current disclosure relates to phenotypic indications of MET (involution of fibroblastic process, and the emergence of foci and cobblestone morphologies). In one embodiment, MET was accelerated by our invention using enhanced cocktails, enabling feeder-free reprogramming using the 6-factor $M_3O$ cocktail without passaging, seeding target cells at a variety of low densities (50K vs. 100K vs. 150K per well). In another embodiment, the cells are seeded at a density gradient with a total cell number ranging from about 15K to 500K cells per well.

One aspect of the current invention relates to the fate of these reprogramming cultures, which proved highly sensitive to the seeding density, presumably because the effects of excessive cytotoxicity and of fibroblastic overgrowth are both self-reinforcing over the course of the transfection regime. In an experiment using "standard" RNA dosing (1200 ng per well), dozens of hESC-like colonies were obtained from HDF-n and XFF fibroblasts plated at 100K per well, while the corresponding 50K and 150K cultures gave only a few colonies after succumbing to a population crash and to fibroblastic overgrowth, respectively. In derivations attempted with two other fibroblast lines, BJ and HDF-a, even the most promising (150K) cultures became virtually quiescent shortly after reaching confluence, subsequently yielding only sporadic colonies with delayed kinetics.

One aspect of the current invention relates to purify the in vitro transcribed mRNAs through size exclusion chromatography to remove aberrant RNA species that may form dsRNA structures, either by themselves or with mRNAs, and provoke cellular immune responses. Using such "cleaned-up" mRNAs—mRNA with reduced cellular immunogenicity, effectively allowed reprogramming of non-human primate cells grown in gradient densities.

In one specific embodiment of the current invention, we switched from ambient to 5% oxygen culture and ramped to full RNA dosing from a quarter dose over the first four days of transfection in an effort to minimize stress-induced cellular senescence.

In one example of the current invention, using these new conditions the inventors tested if substitution of L-Myc for c-Myc could further improve the reprogramming cocktail.

Figure 2:
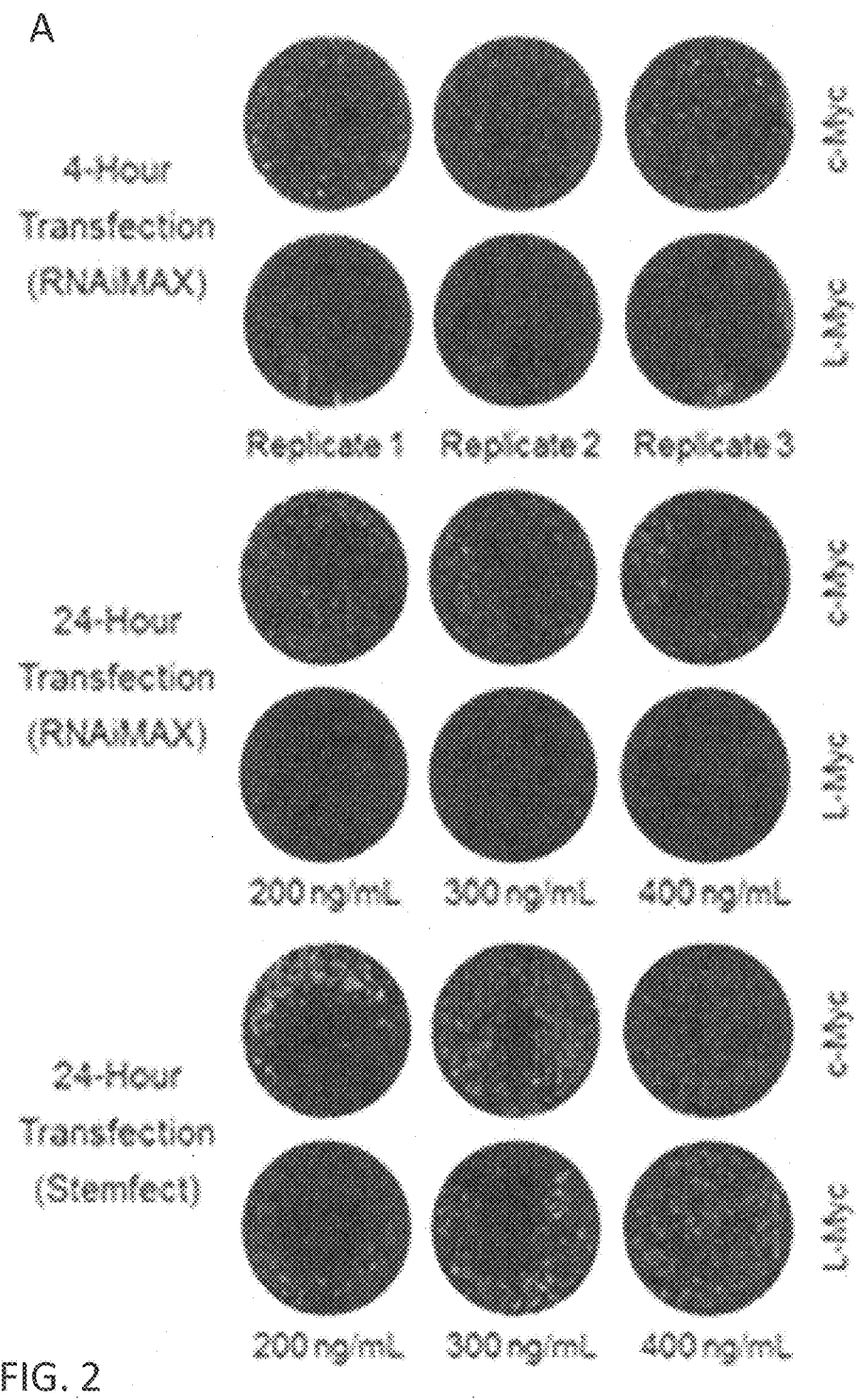
FIG. 2. Feeder-Free Reprogramming Using $M_3O$-Based Cocktail.
Figure 2:
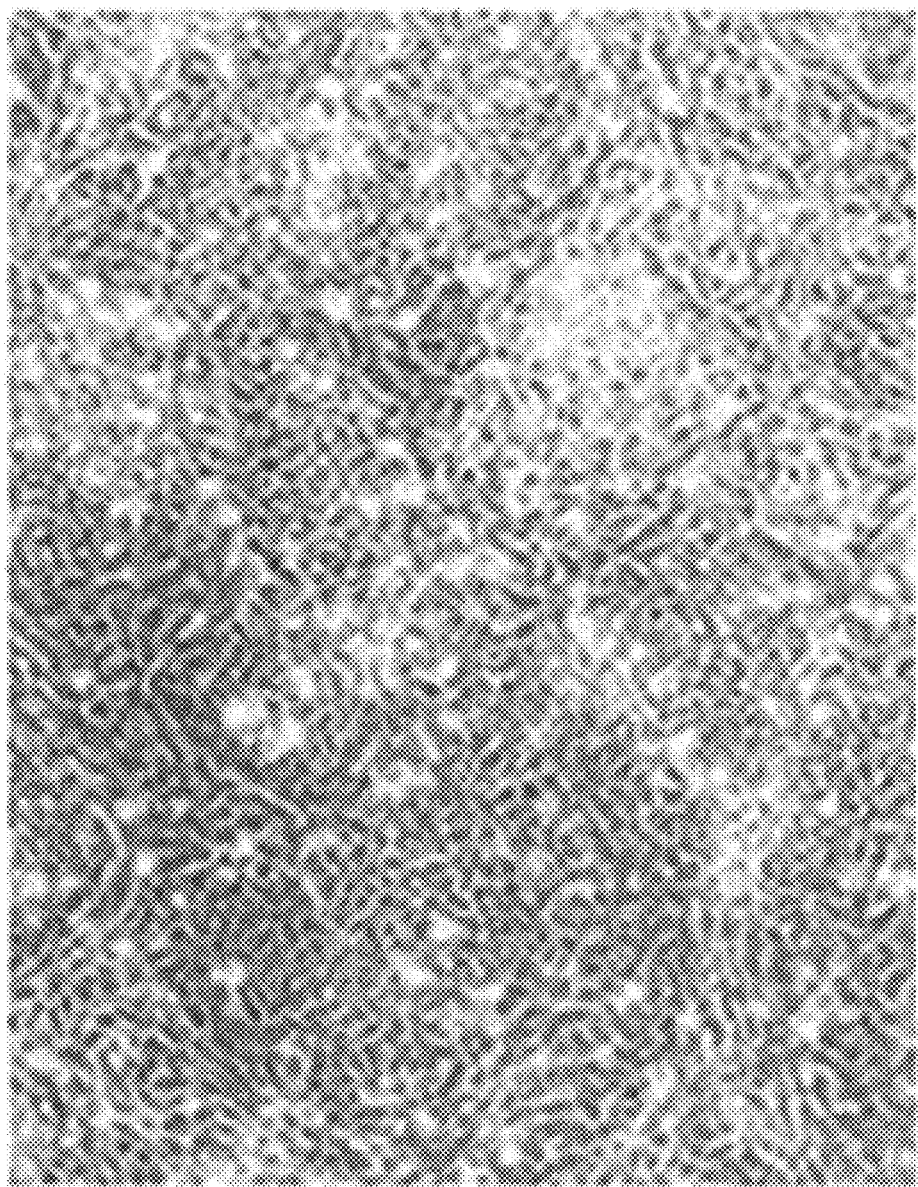
Figure 2:
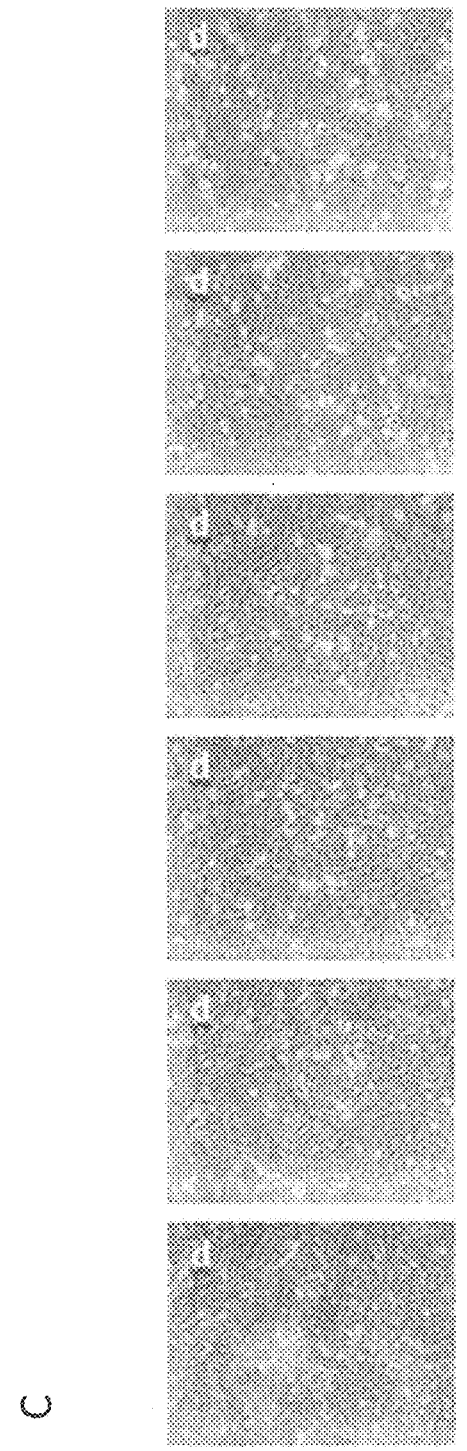

In another embodiment we evaluated a simplified transfection scheme by which RNA was added to cells with daily media changes, rather than being delivered in a separate step four hours earlier. RNA dosing was scaled down in "24-hour transfection" wells to compensate for an expected increase in cytotoxicity, and two different transfection reagents were tested (RNAiMAX and Stemfect). XFF cells were plated at 50K per well and transfected for 9 days. The conventional "4-hour transfection" regime gave on the order of a hundred TRA-1-60[+] colonies per well with the c-Myc-based cocktail, while the L-Myc cocktail performed comparatively poorly (FIG. 2). Results from the "24-hour transfection" cultures were still more impressive. In the most productive of these wells (corresponding to the c-Myc 400 ng/ml Stemfect condition) the culture had become almost overgrown with hESC-like cells on day 9, 24 hours after the last transfection. The mechanistic basis for the superior performance of the "24-hour transfection" might have had the effect of increasing the effective density of thin cultures by concentrating the diffusive factors released by the cells. When these preferred protocol conditions were applied in another example experiments, derivation using HDF-a fibroblasts, in cultures seeded at 75K cells per well the productivity was less spectacular than achieved with the highly proliferative XFF cells, but numerous hESC-like colonies again emerged by as early as day 9 of the protocol (FIG. 4).

In one particular embodiment, when the cells were seeded at lower volume of medium than commonly used volume, e.g. 1 ml, 0.75 ml, 0.5 ml, or the minimum amount of medium that can still sustain cell culture, the efficiency of reprogramming using the above disclosed conditions is clearly improved. such low volume conditions during reprogramming is hereby incorporated in the current invention.

The embodiments that have been described herein by no means are the only applications of the current invention. Those skilled in the art will recognize that the disclosure is also useful for reprogramming other cells under slightly variable conditions or with similar combinations of conventional or engineered factors for reprogramming, directed differentiation, or trans-differentiation.

In other embodiments, optimization of the factor stoichiometry can also enhance the pace of reprogramming—the mRNA method provide the opportunity of defining cocktails which address early and late phases of ipPSC induction independently. The gains obtained from using $M_3O$ provide validation for the recent application of novel, engineered reprogramming factors to iPSC generation. Such engineered reprogramming factors include fusing SOX2, KLF4, CMYC, LMYC, LIN28, NANOG, etc. to transactivation domains from factors other than VP16 OR MYOD, SUCH AS GAL4, GATA1, P53, etc. The reagents and methodology used to deliver mRNA can also be used to co-transfect siRNA and miRNA, which have already proven their worth in iPSC generation. Nonetheless, the feeder-free protocol disclosed herein represents a substantial advance over current protocols, reducing the time required for reprogramming by as much as a half with an equal or greater reduction in labor and materials costs, taking troublesome steps out of the procedure, and allowing mRNA to be delivered to cells with almost the same ease as growth factors or cytokines—i.e., as a media supplement.

In some embodiments, cells are reprogrammed to modulate the immune response. For example, lymphocytes can be reprogrammed into regulatory T cells which can be administered to a patient in need thereof to increase or transfer immune tolerance, especially self-tolerance. The induction or administration of Foxp3 positive T cells may be useful in reducing autoimmune responses such graft rejection, and/or reducing, inhibiting or mitigating one or more symptoms of an autoimmune diseases or disorder such as diabetes, multiple sclerosis, asthma, inflammatory bowel disease, thyroiditis, renal disease, rheumatoid arthritis, systemic lupus erythematosus, alopecia greata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, Grave's disease, Guillain-Barre, Hashimoto's thyroiditis, idiopathic pulmonary fibrosis, idiopathic thmmbocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

The methods can be used to generate cells which may be useful in the treatment of a variety of diseases and disorders, including, but not limited to, diseases such as Parkinson's, Alzheimer disease, wound healing, and multiple sclerosis. The methods are also useful for organ regeneration, and for restoration or supplementation of the immune system. For example, cells at different stages of differentiation such as iPS cells, hematopoietic stem cells, multipotent cells or unipotent cells such as precursor cells, for example, epithelial precursor cells, and others can be administered intravenously or by local surgery. The methods can be used in combination with other conventional methods, such as a prescription medication regime, surgery, hormone therapy, chemotherapy and/or radiotherapy.

In one embodiment, a kit includes RNAs, cells, and a means for transfecting the RNA into the cells. The RNAs can be lyophilized or in solution. Kits may optionally include other materials such as cell culture reagents. In an alternative embodiment, a kit provides re-differentiated, dedifferentiated, or reprogrammed cells prepared according to the disclosed methods, and stored and/or shipped refrigerated or frozen for later use. Cells are typically stored in a solution maintaining viability. Kits containing cells should be stored or shipped using a method consistent with viability such as in a cooler containing dry ice so that cells are maintained below 4° C., and preferably below −20° C.

The kits optionally include one or more of the following: bioactive agents, media, excipients and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. Components of the kit may be packaged individually and can be sterile. The kits are generally provided in a container, e.g., a plastic, cardboard, or metal container suitable for commercial sale. Any of the kits can include instructions for use. The methods can be used to generate cells which may be useful in the treatment of a variety of diseases and disorders, including, but not limited to, neurodegenerative diseases such as Parkinson's, Alzheimer disease, and multiple sclerosis. The methods disclosed herein are also useful for organ regeneration, and for restoration or supplementation of the immune system. For example, cells at different stages of differentiation such as iPS cells, hematopoietic stem cells, multipotent cells or unipotent cells such as precursor cells, for example, epithelial precursor cells, and others can be administered intravenously or by local surgery. The methods can be used in combination with other conventional methods, such as a prescription medication regime, surgery, hormone therapy, chemotherapy and/or radiotherapy.

Aspects of the disclosure provide culturing systems of stem cells and differentiation methods for producing skin tissue cells for wound treatment, and stem cell therapy for the treatment of arthritis, Lupus, and other autoimmune-related diseases.

EXAMPLES

The invention is now described with reference to the following Examples. These Examples are provided for the purpose of illustration only, and the invention is not limited to these Examples, but rather encompasses all variations that are evident as a result of the teaching provided herein.

Example 1—Generation of IVT Templates

Plasmid constructs for generating linear PCR-product in vitro transcription (IVT) templates were constructed using Ligation Independent Cloning (LIC). We first constructed a parental plasmid (pIVT) incorporating 5' and 3' untranslated regions (UTRs) flanking an insertion site designed to accept an open reading frame (ORF) insert encoding a protein of interest. The ORF-flanking sequences are as described in Warren et al, Cell Stem Cell, 2010, comprising a low secondary structure leader and strong Kozak site (5' UTR) and the murine α-globin 3' UTR. A linearized version of the PIVT vector bearing 5' overhangs was produced by reannealing of two PCR products amplified from the plasmid using tailed primers. ORF PCR products with complementary overhangs were produced by an analogous procedure, pooled with the vector PCR products and transformed into DH5a bacteria by heat shock to clone gene-specific constructs (pIVT-KLF4, etc.). The resulting plasmids were used to template PCR reactions to make linear IVT templates incorporating a T7 promoter, UTR-flanked ORF and a T120 tail (SEQ ID NO: 1) to drive addition of a polyA tail, as described in Warren et al, Cell Stem Cell, 2010. The T120 tail (SEQ ID NO: 1) region was introduced through the use of a tailed reverse primer (T120CTTCCTACTCAGGCTTTATTCAAAGACCA) (SEQ ID NO: 2). For the M30 and VPx3 fusion constructs, the transactivating domain-encoding sequences were appended to the ORFs by PCR using tailed primers. PCR product template stocks were maintained at a concentration of ~100 ng/uL.

Example 2—Production of mRNA Cocktails

The mRNA synthesis process is summarized in FIG. 5. Synthetic mRNA was generated in IVT reactions using a 4:1 ratio of ARCA cap analog to GTP to generate a high percentage of capped transcripts. Full substitution of 5m-CTP for CTP and Pseudo-UTP for UTP in the nucleotide triphosphate (NTP) mix was employed to reduce the immunogenicity of the RNA products. Cap analog and modified NTPs were purchased from Trilink Biotechnologies. A 2.5× NTP mix was prepared (ARCA:ATP:5m-CTP:GTP:Pseudo-UTP at 15:15:3.75:3.75:3.75 mM) to replace the standard NTPs provided with the MEGAscript T7 Kit (Ambion) used to perform IVT reactions. Each 40 uL IVT reaction comprised 16 uL NTP mix, 4 uL 10× T7 Buffer, 16 uL DNA template and 4 uL T7 enzyme. Reactions were incubated 4-6 hours at 37° C. and then treated with 2 uL TURBO DNase for a further 15 minutes at 37° C. before being purified on MEGAclear (Ambion) spin columns, the RNA products being eluted in a volume of 100 uL. To remove immunogenic 5' triphosphate moieties from uncapped transcripts, 10 uL of Antarctic Phosphatase reaction buffer and 3 uL of Antarctic Phosphatase (NEB) was added to each prep. Phosphatase reactions were incubated for 30 minutes at 37° C. and the IVT products were repurified. RNA yield was quantitated by Nanodrop (Thermo Scientific), and the preps were consequently adjusted to a standardized working concentration of 100 ng/uL by addition of TE pH 7.0 (Ambion). RNA cocktails were assembled by pooling preps representing the various RFs in the desired stoichiometric ratios. The fraction of each RF used took into account the predicted molecular weight of the respective transcript, all RFs being equimolar except for Oct4 and its derivatives, which were included at 3× molar concentration. A 10% spike of mRNA encoding a short-lived nuclearized monomeric LanYFP fluorescent protein was added to the cocktails to facilitate monitoring of transfection efficacy during reprogramming trials. In other embodiments, mRNAs were also produced by using 2-Thio-Uracil at 25% or 10% of total Uracil (see FIG. 6).

Example 3—Cells and Culture Media

Cells targeted for reprogramming included BJ neonatal fibroblasts (ATCC), HDF-f fetal fibroblasts, HDF-n neonatal fibroblasts and HDF-a adult fibroblasts (ScienCell), and XFF xeno-free neonatal fibroblasts (Millipore). Expansion culture was carried out in BJ medium (DMEM+10% FBS), ScienCell Fibroblast Medium, and FibroGRO Xeno-Free Human Fibroblast Expansion Medium (Millipore) for the BJ, HDF and XFF cells respectively. Feeder cells used were 3001G irradiated neonatal human foreskin fibroblasts (GlobalStem) and FibroGRO mitomycin C-inactivated xeno-free human neonatal fibroblasts (Millipore). Cell passaging steps pertinent to xeno-free feeder-based and feeder-free reprogramming trials were performed using TrypLE Select (Gibco), an animal product-free cell dissociation reagent.

Example 4—Reprogramming of Human Fibroblasts

All reprogramming experiments described were conducted in 6-well tissue culture plates coated with CELLstart (Gibco) xeno-free substrate in accordance with the manufacturer's directions. GlobalStem feeders were plated at 250K per well in the initial BJ reprogramming experiments, using FBS-containing BJ media. In some of the later feeder-based trials, the seeding density was increased and feeders were supplemented ad hoc during media changes in an effort to sustain near-confluent feeder layers in response to the high attrition rates encountered using novel RF cocktails. Xeno-free feeders, when used, were plated in Pluriton-based reprogramming media without serum. Target cells were plated in Pluriton serum-free media (Stemgent) plus antibiotics, Pluriton Supplement and 200 ng/ml B18R interferon inhibitor (eBioscience). Media was replaced daily during and after reprogramming, with B18R supplementation being discontinued the day after the final transfection. In experiments in which cells were split onto fresh feeders during reprogramming, 10 uM Y27632 (Stemgent) was included in the media used for replating. Transfections commenced the day after seeding of target cells, and were repeated at 24-hour intervals for the durations indicated in the text. An RNA dose of 1200 ng was delivered to each well using RNAiMAX (Invitrogen) 4 hours prior to daily media change, except as otherwise noted. RNAiMAX-based transfection cocktails were made up by diluting 100 ng/uL RNA 5× in calcium/magnesium-free DPBS and 5 uL of RNAiMAX per ug of RNA 10× in the same diluent, pooling to produce a 10 ng/uL RNA/vehicle suspension and dispensing to culture media after a 15-minute room temperature incubation. For transfections using Stemfect reagent (Stemgent), RNA and Stemfect (4 uL per ug of RNA) were mixed in Stemfect buffer to give an RNA concentration of 10 ng/uL. The mixture was incubated for 15 minutes, then delivered to culture media or refrigerated for later use.

In other embodiments, reprogramming of human fibroblasts were also performed in media other than pluriton, e.g. Allele's Reprogramming media (see FIG. 7). In some experiments, B18R was not used at all, in other experiments, it was used only in some of the transfections.

Example 5—Characterization of iPSC Colonies

To assess iPSC colony productivity, reprogramming cultures were fixed using 4% paraformaldehyde in DPBS (with calcium/magnesium) and immunostained with StainAlive TRA-1-60 Alexa 488 antibody (Stemgent) diluted 100× in DPBS (with calcium/magnesium). Colony picking, expansion, and subsequent immunostaining and trilineage differentiation assays for molecular and functional validation of pluripotency were performed. DNA fingerprinting and karyotype analyses were conducted. Teratoma formation was performed and confirmed in more than one set of mouse models. Thereby demonstrating the pluripotency of the stem cells.

they have not been in contact with any virus or vector. Utility of the invention can be found in virtually all areas that involve stem cell establishment, differentiation, utility in cellular and developmental research, as well as clinical applications. Similar procedures can also be useful in directed differentiation or trans differentiation.

Example 6—Reprogramming of Cynomolgus Monkey Fibroblasts

The reprogramming experiments using cynomolgus monkey fibroblasts were conducted in 6-well tissue culture plates coated with CELLstart (Gibco) substrate in accordance with the manufacturer's directions. Target cells were plated in Allele Biotech's serum-free media plus antibiotics. Media was replaced daily during and after reprogramming with 2-Thio-modified mRNA/transfection reagent mix delivered together with the fresh media for 12 consecutive days with or without the use of B18R (FIG. 8). Colonies of monkey iPSCs started to appear in day 9, and reached a stage of mature, compact colony stage on day 12.

SEQUENCE LISTING

```
<160> NUMBER OF SEQ ID NOS: 2

<210> SEQ ID NO 1
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttttttttt tttttttttt tttttttttt tttttttttt tttttttttt tttttttttt      60
tttttttttt tttttttttt tttttttttt tttttttttt tttttttttt tttttttttt     120

<210> SEQ ID NO 2
<211> LENGTH: 149
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttttttttt tttttttttt tttttttttt tttttttttt tttttttttt tttttttttt      60
tttttttttt tttttttttt tttttttttt tttttttttt tttttttttt tttttttttt     120
cttcctactc aggctttatt caaagacca                                        149
```

A novel method is disclosed for highly efficient reprogramming of non-stem cells into pluripotent stem cells by contacting target cells with combinations of engineered reprogramming factors and non-engineered reprogramming factors in such a way that iPSCs can be produced in about 9 days, sometimes as short of 6, or even 5 days. These iPS cells can be produced as feeder-free, xeno-free, and footprint-free iPSCs. In addition to the dramatically increased efficiency of reprogramming by the invented process, the novel technology also differs from all previously known technologies in that the iPSCs so created are "clean" in that

What is claimed is:

1. A method for dedifferentiating or reprogramming feeder-free, xeno-free and integration-free mammalian somatic cells to produce feeder-free, xeno-free and integration-free induced pluripotent stem cells comprising:
   a) seeding mammalian somatic cells in a volume of 0.5 ml to 1 ml of xeno-free culture medium on a feeder-free and xeno-free surface;
   b) plating the mammalian somatic cells from step a) at a cell density of 15,000 cells/ml to 500,000 cells/ml;
   c) transfecting the plated mammalian somatic cells from step b) with a composition comprising:

1) one ml or less of xeno-free culture medium:
2) an effective amount of a fusion product between a synthetic mRNA encoding OCT4 and an N-terminal-linked transactivation domain, and
3) synthetic mRNA reprogramming factors encoding SOX2 KLF4, NANOG, and optionally c-MYC or LIN28, wherein the synthetic mRNA reprogramming factors are provided at a concentration of up to about 800 ng/ml;
d) culturing said somatic cells with the composition from step c) under feeder-free and xeno-free culture conditions until the media is changed once daily; and
e) repeating step d) until the mammalian somatic cells are reprogrammed or de-differentiated to produce feeder-free, xeno-free and integration-free induced pluripotent stem cells.

2. The method of claim 1, wherein the synthetic mRNAs are purified to remove any contaminating non-mRNA species from transcription.

3. The method of claim 1, wherein the cells in step a) are seeded in a density gradient.

4. The method of claim 1, wherein the mammalian somatic cells are non-human primate cells.

5. The method of claim 1, wherein the mammalian somatic cells are cynomolgus monkey cells.

6. The method of claim 1, wherein the mammalian somatic cells are rhesus monkey cells.

7. The method of claim 1, wherein the mammalian somatic cells are baboon cells.

8. The method of claim 1, wherein the mammalian somatic cells are canine cells.

9. The method of claim 1, wherein the mammalian somatic cells are equine cells.

10. The method of claim 1, wherein the mammalian somatic cells are bovine cells.

11. The method of claim 1, wherein the mammalian somatic cells are swine cells.

12. The method of claim 1, wherein the cells mammalian somatic are ovine cells.

13. The method of claim 1, wherein OCT4 is fused to an N-terminal MyoD transactivation domain in tandem triplicates.

14. The method for reprogramming mammalian somatic cells of claim 4, wherein steps d) and e) of the method further comprises transfecting the cells with varying doses of about 50 ng/ml to 800 ng/ml of synthetic mRNA reprogramming factors during each medium change, wherein lower doses of the synthetic mRNA reprogramming factors are used at earlier time points than later time points.

15. The method of claim 4, wherein in step b) of the method further comprises plating the cells on a feeder-free surface at a cell density of about 15,000 cells/ml; 25,000 cells/ml; 50,000 cells/ml; 75,000 cells/ml; 100,000 cells/ml; or 150,000 cells/ml in xeno-free culture medium and culturing the non-human primate cells under feeder-free, xeno-free and integration-free conditions; and;
wherein step c) of the method further comprises transfecting the cells with varying doses of about 50 ng/ml to about 800 ng/ml of synthetic mRNA reprogramming factors during each medium change, wherein lower doses of the synthetic mRNA reprogramming factors are used at earlier time points than later time points.

16. The method for reprogramming non-human mammalian somatic cells of claim 4, wherein step b) of the method further comprises:
1) plating the cells at a density of about 15,000 cells/ml; 25,000 cells/ml; 50,000 cells/ml; 75,000 cells/ml; 100,000 cells/ml; or 150,000 cells/ml in xeno-free culture medium and culturing the non-human primate cells under feeder-free, xeno-free and integration-free conditions wherein the volume of each surface is between 0.5 ml to 1 ml of xeno-free culture medium; and
wherein step c) of the method further comprises transfecting the cells with varying doses of about 50 ng/ml to about 800 ng/ml of synthetic mRNA reprogramming factors during each medium change, wherein lower doses of the synthetic mRNA reprogramming factors are used at earlier time points than later time points.

17. The method of claim 1, wherein the induced pluripotent stem cells are maintained in culture.

18. The method of claim 1, further comprising differentiating the induced pluripotent stem cells.

19. The method of claim 2, wherein the composition further comprises Rarg and LrH 1 transactivation domains.

20. The method of claim 1, wherein the fusion product comprises a synthetic mRNA encoding OCT4 fused to a VP16 transactivation domain.

* * * * *